(12) United States Patent
Baron et al.

(10) Patent No.: US 9,664,682 B2
(45) Date of Patent: May 30, 2017

(54) ASSAY TO MEASURE MIDKINE OR PLEIOTROPHIN LEVEL FOR DIAGNOSING A GROWTH

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Jeffrey Baron, North Potomac, MD (US); Youn Hee Jee, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/646,078

(22) PCT Filed: Nov. 15, 2013

(86) PCT No.: PCT/US2013/070305
§ 371 (c)(1),
(2) Date: May 20, 2015

(87) PCT Pub. No.: WO2014/081633
PCT Pub. Date: May 30, 2014

(65) Prior Publication Data
US 2015/0301057 A1 Oct. 22, 2015

Related U.S. Application Data

(60) Provisional application No. 61/728,624, filed on Nov. 20, 2012, provisional application No. 61/815,342, filed on Apr. 24, 2013.

(51) Int. Cl.
G01N 33/53 (2006.01)
G01N 33/574 (2006.01)

(52) U.S. Cl.
CPC . *G01N 33/57488* (2013.01); *G01N 2333/475* (2013.01)

(58) Field of Classification Search
CPC ....... G01N 33/57488; G01N 2333/475; G01N 33/50; G01N 33/53; G01N 2800/00
See application file for complete search history.

(56) References Cited

U.S. PATENT DOCUMENTS

| 4,444,879 | A | * | 4/1984 | Foster | ......... | G01N 33/545 422/400 |
|---|---|---|---|---|---|---|
| 7,056,692 | B2 | | 6/2006 | Deuel | | |
| 7,090,983 | B1 | | 8/2006 | Muramatsu et al. | | |
| 7,888,485 | B2 | | 2/2011 | Tso et al. | | |
| 2003/0149534 | A1 | | 8/2003 | Shinozawa et al. | | |
| 2007/0154949 | A1 | | 7/2007 | Mitsumoto et al. | | |
| 2011/0159022 | A1 | | 6/2011 | Kerzerho et al. | | |
| 2011/0159498 | A1 | | 6/2011 | Kao et al. | | |
| 2011/0312520 | A1 | | 12/2011 | Kennedy et al. | | |

FOREIGN PATENT DOCUMENTS

| CN | 102565383 A | 7/2012 |
|---|---|---|
| WO | WO 00/31541 A2 | 6/2000 |
| WO | WO 2007053659 A2 | 5/2007 |
| WO | WO 2009/067546 A2 | 5/2009 |
| WO | WO 2011/143361 A2 | 11/2011 |
| WO | WO 2012/178058 A1 | 12/2012 |

OTHER PUBLICATIONS

Ameur et al., Aggressive inherited and sporadic medullary thyroid carcinomas display similar oncogenic pathways, Endocrine-Related Cancer, 2009, 16, pates 1261-1272.*
Jager et al., Serum levels of the angiogenic factor pleiotrophin in relation to disease stage in lung cancer patients, British Journal of Cancer, 2002, 86, pp. 858-863.*
Kato et al., A new assay for thyroglobulin concentration in serum using monoclonal antibodies against synthetic peptides, Clinica Chimica Acta 298, 2000, pp. 69-84.*
Aigner et al., "Marked Increase of the Growth Factors Pleiotrophin and Fibroblast Growth Factor-2 in Serum of Testicular Cancer Patients," *Ann. Oncol.*, 14 (10), 1525-1529 (2003).
Huang et al., "Gene Expression in Papillary Thyroid Carcinoma Reveals Highly Consistent Profiles," *Proc. Natl. Acad. Sci. USA*, 98 (26), 15044-15049 (2001).
Ikematsu et al., "Serum midkine levels are increased in patients with various types of carcinomas," *Br. J. Cancer*, 83 (6), 701-706 (2000).
International Preliminary Report on Patentability, Application No. PCT/US2013/070305, dated Jun. 4, 2015.
International Search Report, Application No. PCT/US2013/070305, dated Apr. 16, 2014.
Kato et al., "Immunohistochemical and in situ hybridization analyses of midkine expression in thyroid papillary carcinoma," *Mod. Pathol.*, 13 (10), 1060-1065 (2000).

(Continued)

*Primary Examiner* — Gary W Counts
(74) *Attorney, Agent, or Firm* — Leydig, Voit & Mayer, Ltd.

(57) ABSTRACT

The invention provides methods and kits for diagnosing a growth in a subject by providing a sample of a growth taken from a subject, determining the level of midkine or pleiotrophin in the sample by an immunoassay, and comparing the level of midkine or pleiotrophin determined from the sample with a control. An increased level of midkine or pleiotrophin in the sample as compared to the control is diagnostic of a malignant growth, whereas an equivalent or decreased level of midkine or pleiotrophin in the sample as compared to the control is diagnostic of a benign growth. Growth refers to, for example, papillary thyroid cancer (PTC).

9 Claims, 6 Drawing Sheets

(56) References Cited

OTHER PUBLICATIONS

Kato et al., "Midkine Expression in Reed-Sternberg Cells of Hodgkin's Disease," *Leuk Lymphoma*, 37 (3-4), 415-424 (2000).
Muramatsu, "Midkine, a heparin-binding cytokine with multiple roles in development, repair and diseases," *Proc. Jpn. Acad. Ser. B. Biol. Sci.*, 86 (4), 410-425 (2010).
Muramatsu, "Midkine and pleiotrophin: two related proteins involved in development, survival, inflammation and tumorigenesis," *J. Biochem.*, 132 (3), 359-371 (2002).
Tsutsui et al., "A New Family of Heparin-Binding Growth/Differentiation Factors: Increased Midkine Expression in Wilms' Tumor and Other Human Carcinomas," *Cancer Res.*, 53 (6), 1281-1285 (1993).
Written Opinion of the International Searching Authority, Application No. PCT/US2013/070305, dated Apr. 16, 2014.
Jee et al., "Increased Pleiotrophin Concentrations in Papillary Thyroid Cancer," *PLoS One*, 11(2), 1-11 (2016).
Jee et al., "Midkine concentrations in fine-needle aspiration of benign and malignant thyroid nodules," *Clin. Endocrinol.*, 83 (6), 977-984 (2015).
Office Action, Chinese Patent Application No. 2013800706225, dated Mar. 31, 2016, 19 pages.
Bao et al. "Developing and evaluating fast detection ELISA kit for human serum soluble CD40 ligand" *Guangdong Medical*, 28(2) pp. 187-189, Feb. 28, 2007.
Liu et al. "Study of Expression of Midkine in Thyroid Gland Carcinoma" *Hei Long Jiang Medical Journal*, 32(5) pp. 321-322, May 31, 2008.
Lui et al. "The Study of oncogene c-fos expression in papillary thyroid carcinoma by use of β-actin as a normalization parameter" *Journal of Tianjin Medical University* vol. 8, issue 1, pp. 7-10 (Mar. 30, 2002).
Nakagawara et al., "Differential Expression of Pleitotrophin and Midkine in Advanced Neuroblastomas" *Cancer Research* 55:1792-1797 (Apr. 15, 1995).
Sato et al. "Midkine antisense oligodeoxyribonucleotide inhibits renal damage induced by ischemic reperfusion" *Kidney International* 67:1330-1339 (Dec. 31, 2005).
Office Action, Chinese Patent Application No. 2013800706225, dated Feb. 4, 2017, 27 pages.
European Patent Office, Communication pursuant to Rule 164(2)(b) and Article 94(3) EPC, EP 13798508.1, dated Feb. 27, 2017, 9 pages.
Kihara et al. "Final Pathology Findings After Immediate or Delayed Surgery in Patients with Cytologically Benign or Follicular Thyroid Nodules" *World Journal of Surgery: Offical Journal of the International Society of Surgery* 35(3): 558-562 (Dec. 24, 2010).
Nakanishi et al. "Expression of Midkine and Pleitotropin in Ovarian Tumors" *Obstetrics and Gynocology* 90(2):285-290 (Aug. 1, 1997).
Shmizu et al. "The Clinical Utility of Lens Culinaris Agglutinin-reactive Thyroglobulin Ratio in Serum for Distinguishing Benign from Malignant Conditions of the Thyroid" *Clinica Chimica Acta* 379(1-2): 101-104 (Apr. 1, 2007).

\* cited by examiner

ASSAY TO MEASURE MIDKINE OR PLEIOTROPHIN LEVEL FOR DIAGNOSING A GROWTH

CROSS-REFERENCE TO RELATED APPLICATIONS

This patent application is a U.S. National Phase Application of International Patent Application No. PCT/US2013/070305, filed Nov. 15, 2013, which claims the benefit of U.S. Provisional Patent Application No. 61/815,342, filed Apr. 24, 2013 and U.S. Provisional Patent Application No. 61/728,624 filed Nov. 20, 2012, each of which is incorporated by reference herein in its entirety.

BACKGROUND OF THE INVENTION

Cancer is a leading cause of death worldwide. Survival rates for many cancers can be improved by early detection and treatment. However, for many cancers, diagnostic approaches are highly invasive, for example, involving surgical biopsy. Less invasive methods, such as needle biopsies, are often less reliable. More reliable methods of cancer detection are desired, as are less invasive methods of detection.

Midkine, also known as MK, MDK, and NEGF2, is a 13-kDa heparin-binding growth factor rich in basic amino acids and cysteine which affects growth, survival, migration, and gene expression of various target cells. Human midkine is encoded by the MDK gene. Expression of the MDK gene is induced by retinoic acid or hypoxia, and suppressed by glucocorticoid. Expression of MDK is high during midgestation, but low or absent in most adult tissues (Muramatsu et al., *Proc. Jpn. Acad., Ser. B*, 86: 410-425 (2010)).

MDK gene expression is increased in Wilms' tumor specimens and in human stomach, colon, pancreatic, lung, and esophageal carcinoma cell lines (Tsutsui et al., *Cancer Res.*, 53: 1281-1285 (1993)). Serum levels of midkine are increased in patients with esophageal, gastric, duodenal, colon, hepatocellular, bile duct/gallbladder, pancreatic, thyroid, or lung carcinoma (Ikematsu et al., *Brit. J. Cancer*, 83(6): 701-706 (2000)). In situ hybridization and immunohistochemical analyses demonstrated that MDK expression and midkine production are increased in human thyroid papillary carcinoma specimens (Kato et al., *Mod. Pathol.*, 13(10): 1060-1065 (2000)).

Improved methods, compositions, and kits for detecting midkine expression in a biological sample are desired, which may be useful for diagnostic and prognostic purposes in proliferative disorders, such as cancer.

BRIEF SUMMARY OF THE INVENTION

The invention provides a method for diagnosing a growth in a subject which includes providing a sample of a growth obtained from a subject, analyzing the sample by an immunoassay to determine the level of midkine, and comparing the level of midkine determined from the sample with a control. The level of midkine determined from the sample relative to the control is diagnostic of a benign growth or a malignant growth.

The invention also provides a kit for diagnosing a growth in a subject. The kit includes an antibody that specifically binds to midkine, and instructional material for determining, by an immunoassay, the level of midkine in a sample of a growth obtained from a subject as compared to a control.

BRIEF DESCRIPTION OF THE SEVERAL VIEWS OF THE DRAWING(S)

Figure 3:
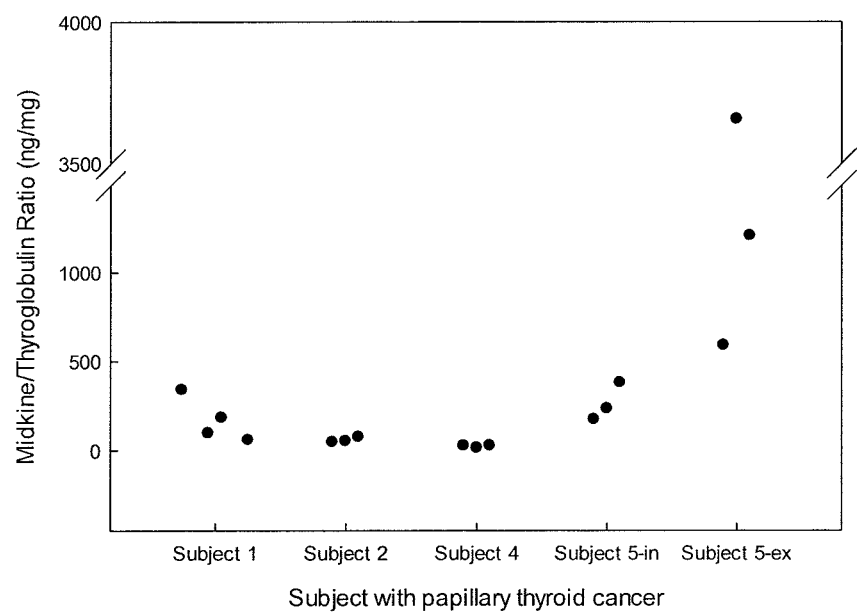

FIG. 3 is a dot plot depicting the variability of MK/Tg ratio among individual FNA samples from the same papillary thyroid cancer. The MK/Tg values of 3-4 individual passages from each of 4 subjects with PTC are shown. Subject 5 had FNA samples both in vivo, preoperatively (Subject 5-in,) and ex vivo, immediately after thyroidectomy (Subject 5-ex).

Figure 4:
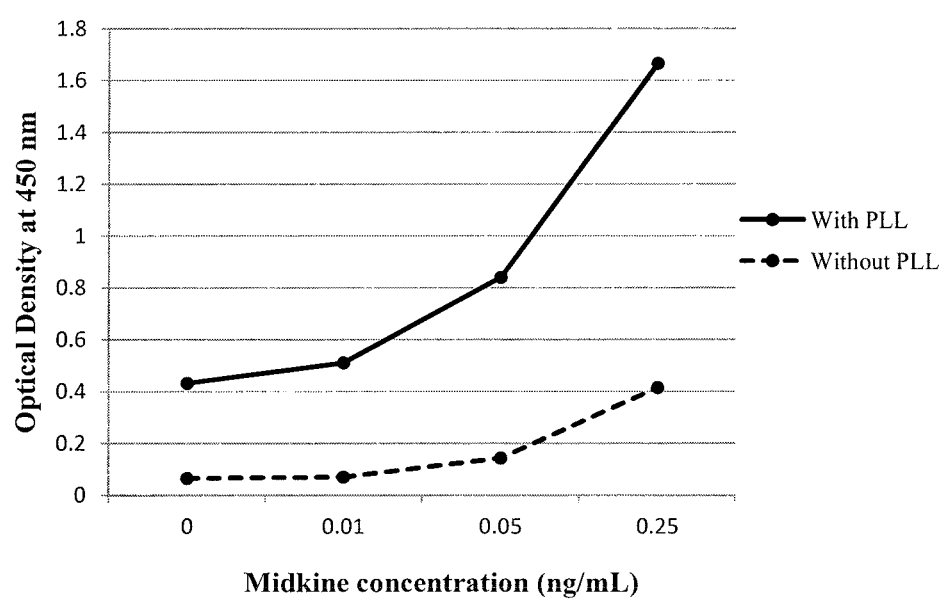

FIG. 4 is a line graph depicting the absorbance of samples of recombinant midkine protein of known concentration as detected by sandwich enzyme-linked immunosorbent assay (ELISA) performed in the presence or absence of 10 μg/mL poly-L-lysine (PLL) in the detection antibody solution.

Figure 5:
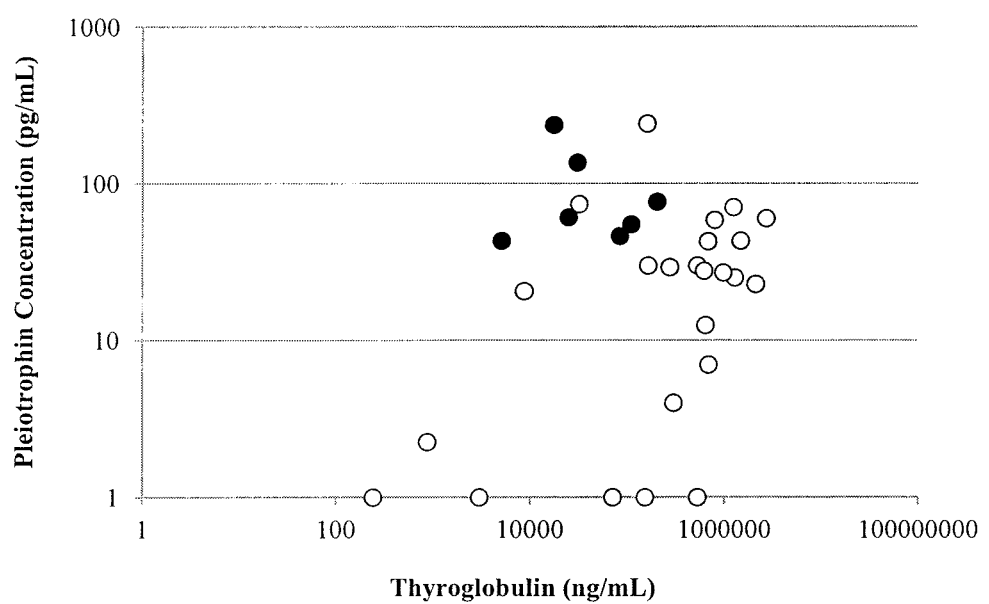

FIG. 5 is a dot plot depicting pleiotrophin and thyroglobulin concentrations in ex vivo FNA samples of histologically confirmed benign thyroid nodules (open circles) or PTC tissue (closed circles).

Figure 6A:
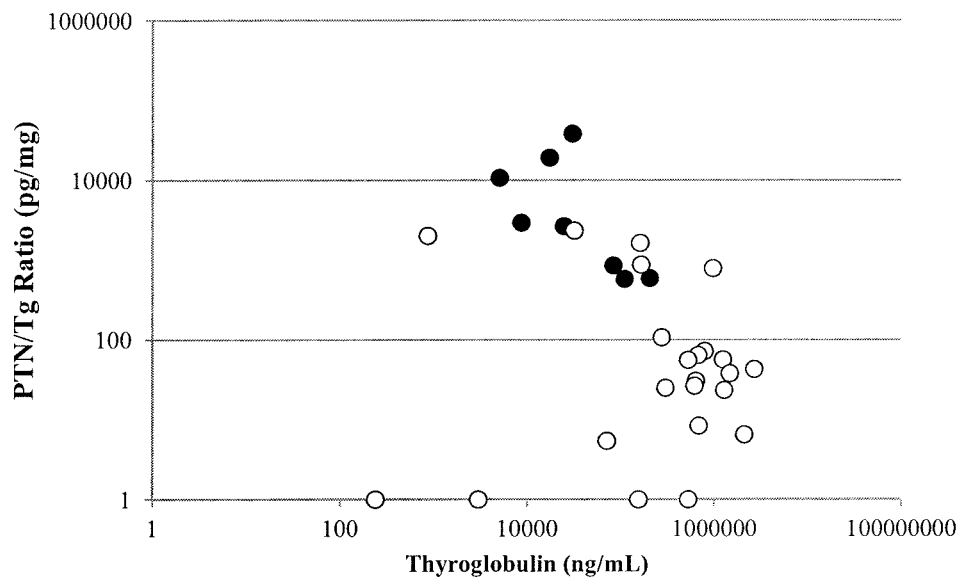

FIG. 6A is a dot plot depicting pleiotrophin to thyroglobulin (PTN/Tg) ratios in ex vivo FNA samples of benign thyroid nodules (open circles) or PTC tissue (closed circles).

Figure 6B:
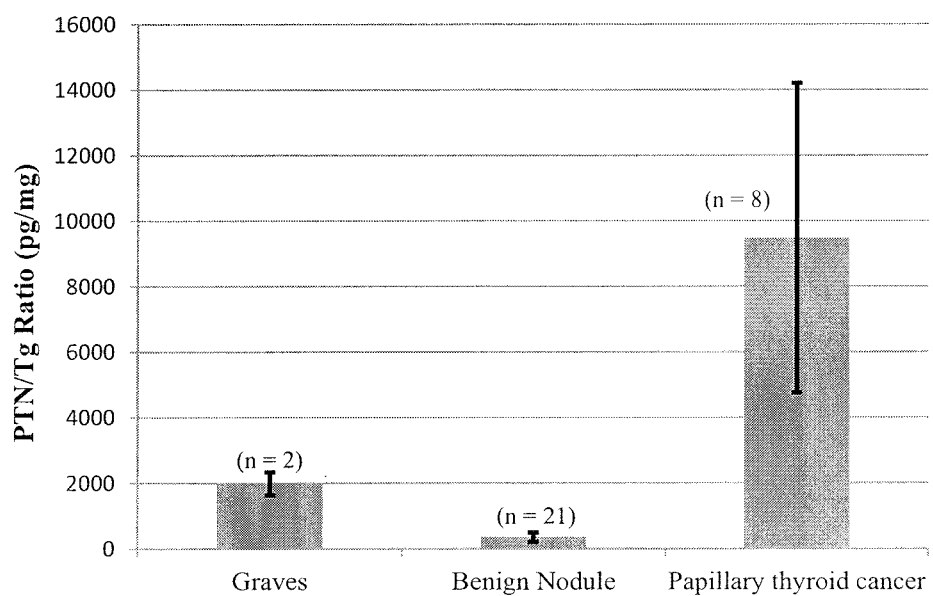

FIG. 6B is a bar graph depicting PTN/Tg ratios (mean±SEM) in ex vivo FNA samples of benign thyroid nodules or PTC tissue, wherein benign nodules from patients with Graves' disease are separated from total benign nodules.

DETAILED DESCRIPTION OF THE INVENTION

The invention provides methods and kits for determining whether a growth is benign or malignant based upon the level of midkine present in a sample of the growth.

In one aspect, the invention provides a method for diagnosing a growth in a subject. The method comprises (a) providing a sample of a growth obtained from a subject, (b) analyzing the sample by an immunoassay to determine the level of midkine, and (c) comparing the level of midkine determined from the sample with a control. The level of midkine determined from the sample as compared with the control is diagnostic of a benign growth or a malignant growth.

In another aspect, the invention provides a kit for diagnosing a growth in a subject. The kit comprises (a) an antibody that specifically binds to human midkine, and (b) instructional material for determining the level of midkine by an immunoassay in a sample of a growth from a subject as compared with a control. The level of midkine determined from the sample as compared with the control is diagnostic of a benign growth or a malignant growth.

The term "growth" as used herein refers to an abnormal mass of tissue. The "growth" can be a solid mass, a fluid-filled cavity, or a mixture of solid and fluid components.

All tumors are growths. The tumor can be a solid tumor or a hematologic tumor. A solid tumor can be derived from any tissue or organ, including but not limited to the kidney, liver, cervix, skin, thyroid, brain, breast, colon, lung, pancreas, prostate, stomach, ovaries, testicles, urinary bladder, bile duct, or gall bladder. A solid tumor also can be derived from bone. Hematologic tumors include leukemia and lymphoma.

In certain embodiments, the growth is a nodule. The term "nodule" refers to an abnormal mass present in an otherwise normal tissue. In some embodiments, the nodule is a thyroid nodule. In other embodiments, the nodule is a lung nodule.

In other embodiments, the growth is a "cyst" or an "abscess" comprised of solid, fluid, or semi-solid components.

In the context of the invention, the sample can be any sample taken from a growth present in an organ or tissue of a subject. The sample can be taken from any suitable region of the growth, such as a region approximating the center of a growth, or a region near the periphery of a growth.

A sample for use in the invention can be taken by any suitable method capable of collecting cells. The sample can be obtained from a surgical or open biopsy, or the sample can be obtained using a needle biopsy. Thus, the sample may be derived from a "punch," "shave," curettage, fine needle aspiration (FNA), core needle sample, sentinel lymph node, or excisional biopsy, or any other method of biopsy known in the art.

In certain preferred embodiments, the sample is obtained by FNA. The sample can be all of the material obtained by FNA, or the sample can be a portion of the material obtained by FNA. For example, the sample can be a "washout" or "rinse" of the material remaining in a FNA needle after expression of the contents of the needle onto a microscope slide for conventional cytological or histological analyses.

The subject can be a human or any suitable non-human mammal such as a mouse, rat, rabbit, cat, dog, pig, sheep, cow, or primate. In some embodiments, the subject is a non-human experimental animal model. In some embodiments, the subject is a primate. Preferably, the subject is a human.

The immunoassay used to determine the level of midkine in a sample is not particularly limited. In some embodiments, the immunoassay is enzyme-linked immunosorbent assay (ELISA), sandwich ELISA, radioimmunoassay, immunoradiometric assay, gel diffusion precipitation reaction, immunodiffusion assay, in situ immunoassay western blot, immunoprecipitation assay, or immunofluorescence assay. In certain preferred embodiments, the immunoassay is a "sandwich ELISA" wherein a surface coated with a first antibody specific for midkine is contacted with a solution containing a sample under conditions in which a stable complex can form between the first antibody and the midkine present in the sample, and the bound midkine is detected with a second antibody specific for midkine using any suitable means in the art, wherein the detection of a complex indicates the presence of midkine in the sample. Methods of performing immunoassays are well-known to those of skill in the art (see, e.g., *Antibodies: A Laboratory Manual*, E. Harlow and D. Lane, ed., Cold Spring Harbor Laboratory (Cold Spring Harbor, N.Y., 1988))

An antibody which "specifically binds" or which is "specific for" midkine refers to any antibody, or fragment or derivative thereof, that recognizes at least one antigen or epitope of midkine and can remain stably bound thereto under standard binding, washing, and detection conditions utilized in an immunoassay. The terms "anti-midkine antibody" and "antibody against midkine" as used herein refer to an antibody which "specifically binds" or which is "specific for" midkine.

The antibody specific for midkine can be a polyclonal antibody, a monoclonal antibody, a chimeric antibody, a single chain of an antibody, or an Fab fragment that binds to midkine. For example, the antibody against midkine can be a monoclonal antibody directed against a single midkine epitope, a combination of monoclonal antibodies directed against different epitopes of a single midkine antigenic component, monoclonal antibodies directed towards epitopes of different midkine antigenic components, polyclonal antibodies directed towards the same midkine antigen, or polyclonal antibodies directed towards different midkine antigens.

The antibody specific for midkine can be prepared by any suitable manner.

A polyclonal antibody can be prepared by immunizing a host animal, e.g., by injection, with a midkine polypeptide or a derivative (e.g., fragment or fusion protein) thereof. Suitable host animals include, but are not limited to, rabbits, mice, rats, sheep, goats, etc. A midkine polypeptide can be produced recombinantly or by chemical synthesis, and a fragment or other derivative or analog thereof, including a fusion protein, can be used as an immunogen to generate an antibody that recognizes the midkine polypeptide. In one embodiment, the midkine polypeptide or fragment thereof can be conjugated to an immunogenic carrier, e.g., bovine serum albumin (BSA) or keyhole limpet hemocyanin (KLH). Adjuvants can be used to increase the immunological response of the host animal, depending on the host species, including but not limited to Freund's (complete and incomplete), mineral gels (such as aluminum hydroxide), surface active substances (such as lysolecithin), pluronic polyols, polyanions, peptides, oil emulsions, keyhole limpet hemocyanins, dinitrophenol, and human adjuvants (such as BCG (bacille Calmette-Guerin) and *Corynebacterium parvum*).

A monoclonal antibody can be prepared by any technique that provides an antibody by a continuous cell line in culture. These techniques include, but are not limited, to the hybridoma technique originally developed by Kohler and Milstein (*Nature*, 256: 495-497 (1975)), as well as the trioma technique, the human B-cell hybridoma technique (Kozbor et al., *Immunol. Today*, 4: 72 (1983); Cote et al., *Proc. Natl. Acad. Sci. USA*, 80: 2026-2030 (1983)), and the EBV hybridoma technique (Cole et al., "The EBV-hybridoma technique and its application to human lung cancer" in *Monoclonal Antibodies and Cancer Therapy*, Alan R. Liss, Inc., pp. 77-96 (1985)). The production of monoclonal antibodies by CDR grafting is described in U.S. Pat. Nos. 5,585,089, 5,693,761, 5,693,762, and 5,225,539. Additionally, monoclonal antibodies can be produced in germ-free animals, as described in International Patent Application Publication No. WO 1989/012690.

A chimeric antibody can be prepared, for example, by splicing the genes from a mouse antibody specific for a midkine polypeptide together with genes from a human antibody of appropriate biological activity (Morrison et al., *J. Bacteriol.*, 159: 870 (1984); Neuberger et al., *Nature*, 312: 604-608 (1984); and Takeda et al., *Nature*, 314: 452-454 (1985)). Techniques for the production of single chain antibodies (as described in, for example, U.S. Pat. Nos. 5,476,786, 5,132,405, and 4,946,778) can be adapted to produce an antibody against midkine.

An antibody fragment, which contains the idiotype of the antibody against midkine, can be generated in any suitable manner, e.g., using known techniques. Suitable antibody fragments include, but are not limited to, a F(ab')$_2$ fragment which can be produced by pepsin digestion of the antibody molecule, a Fab' fragment which can be generated by reducing the disulfide bridges of the F(ab')$_2$ fragment, and a Fab fragment which can be generated by treating an antibody with papain and a reducing agent.

The antibody specific for midkine also can be an anti-midkine antibody known in the art, such as a commercially available anti-midkine antibody obtainable from BioVendor (Czech Republic), Abcam Inc. (Cambridge, Mass.), or R&D Systems Inc. (Minneapolis, Minn.).

In the method of the invention, an antibody against midkine, as bound to midkine present in the sample, is detected so as to determine the level of midkine. The detection of the antibody against midkine can be accomplished by any suitable technique known in the art. In one embodiment, antibody binding is detected by detecting a label conjugated to the antibody against midkine. In another embodiment, the antibody binding is detected by binding of a secondary antibody or reagent to the antibody against midkine, wherein the secondary antibody is labeled and detected.

Any suitable label can be utilized so as to determine the level of midkine present in a sample. Suitable labels include, but are not limited to, an enzyme, (e.g., alkaline phosphatase, horseradish peroxidase, etc.), a fluorescent molecule, a chemiluminescent molecule, a radionuclide, and a dye molecule. Other reagents and materials can be utilized to facilitation determination of the level of midkine present in a sample, such as pretreatment and blocking reagents, amplification reagents (e.g., biotin-streptavidin), wash buffers, blocking reagents, and co-staining reagents. Methods of detecting an antigen-antibody complexes are well-known to those of skill in the art.

In some embodiments, the control is a purified midkine protein produced recombinantly in a host cell. In yet other embodiments, the control is a purified midkine protein isolated from cell or tissue which produces midkine endogenously. Thus, a kit of the invention can include an amount of purified midkine protein useful as a control, e.g., to construct a standard curve for comparison with the level of midkine present in a sample. A control midkine protein can be identical to midkine found in a human or other mammalian cell or tissue, or the control midkine protein can be a modified midkine protein, such as a fusion protein, a truncated protein, or a protein containing amino acid substitutions.

In the method of the invention, the level of midkine present in a sample typically is normalized to the level of a protein or other substance present in the sample. In some embodiments, the level of midkine present in a sample is normalized to the level of a protein encoded by a "housekeeping gene" which is expressed in the sample. The term "housekeeping gene" is well-known in the art as referring to a gene expressed at a relatively constant level during physiological and pathophysiological conditions. A protein encoded by any housekeeping gene can be used to normalize the level of midkine present in a sample. Examples of suitable normalization proteins include, for example, β-actin, Hsp90, and GAPDH. In some embodiments, the protein used to normalize the level of midkine is encoded by a gene which is expressed in a tissue-specific, e.g., organ-specific or tumor-specific, manner. For example, the level of thyroglobulin can be used to normalize the level of midkine present in a thyroid nodule or thyroid tumor. Tissue-specific genes and their protein products are well-known to those of skill in the art. In other embodiments, the substance used for normalization represents a set of related molecules, for example, total protein in the sample. In other embodiments, the substance is not a protein but another component present in a sample, such as a nucleic acid, lipid, carbohydrate, or small organic or non-organic molecule.

Any suitable method known in the art can be used to determine the level of a protein used to normalize the level of midkine in a sample. In some embodiments, the method for determining the level of a normalization protein in a sample is the same as the method for determining the level of midkine in the sample, except that an antibody specific for the normalization protein is substituted for an anti-midkine antibody.

The control can be any suitable comparator. In some embodiments, the control is a sample of normal tissue taken from the same subject having the growth and desirably the same organ from which the growth is obtained. For example, if the growth is a thyroid nodule, the control can be a sample of normal thyroid tissue taken from the subject with the thyroid nodule. In other embodiments, the control is a sample of normal tissue taken from another member of the same species as the subject having the growth, and desirably the same organ from which the growth is obtained. For example, if the growth is a thyroid nodule in a human subject, the control can be a sample of normal thyroid tissue taken from another human subject. The control also can be a historical control, such as a level of midkine determined from a prior sample of a growth obtained from the same subject from which a subsequent sample of a growth is obtained. The subsequent sample can be derived from the same growth as a prior sample, or a different growth. For example, if the growth is a thyroid nodule in a human subject, the control can be a level of midkine determined from a prior sample of a thyroid nodule taken from the same human subject. Preferably, the same method used to normalize the level of midkine in a sample of a growth is used to normalize the level of midkine in a control tissue sample.

In still yet other embodiments, the control is a predetermined midkine level or predetermined set of midkine levels. Thus, in the context of the invention, it is not necessary to perform an assay on a control sample in order to provide a control midkine level. In some embodiments, the predetermined midkine level is determined by previous studies of benign growths, malignant growths, and/or normal tissues in other individuals of the same species from which a sample of a growth is obtained.

The control can be a combination of any two or more of the foregoing controls. Those of skill in the art will understand that the determination of a suitable control will depend upon several factors, such as the tissue origin and predicted malignancy of the growth.

In an embodiment of the method of the invention, the determination of an equivalent or decreased level of midkine in a sample of a growth as compared to a control, especially a benign control, is diagnostic of a benign growth, whereas the determination of an increased level of midkine in a sample of a growth as compared to a known benign control is diagnostic of a malignant growth. The term "benign" refers to a growth which is non-cancerous and lacks the ability to metastasize, whereas the term "malignant" refers to a growth which is cancerous and often has the ability to metastasize. A malignant growth can be of any grade of malignancy, e.g., pre-malignant, low grade, intermediate grade, or high grade. One of ordinary skill in the art understands that grading systems differ for each type of cancer. All technical and scientific terms used herein have the meaning commonly understood by a person skilled in the art to which this invention belongs, unless explicitly stated otherwise.

The "threshold" or "cut-off" value for determining whether a level of midkine determined from a sample is indicative of a benign growth or a malignant growth is variable and will depend upon several factors, such as the tissue origin of the growth, number of samples and controls, and choices of immunoassay and normalization protein. One of ordinary skill in the art can determine an appropriate cut-off value empirically based upon any combination of the foregoing factors.

In certain embodiments, the method and kit of the invention are used to determine whether a thyroid growth is benign or malignant, the normalization protein is thyroglobulin, and the threshold value is 10 nanograms midkine per milligram thyroglobulin. Examples of benign thyroid growths include adenomatoid/colloid nodules, follicular adenomas, and nodules associated with underlying chronic lymphocytic thyroiditis. Examples of malignant thyroid growths include papillary thyroid cancer (PTC), follicular thyroid cancer, medullary thyroid cancer, and anaplastic thyroid cancer.

In other embodiments, the method and kit of the invention are used to diagnose a growth associated with another cancer, including but not limited to acute lymphoblastic leukemia, acute myeloid leukemia, adrenocortical carcinoma, AIDS-related lymphoma, AIDS-related malignancies, anal cancer, cerebellar astrocytoma, extrahepatic bile duct cancer, bladder cancer, osteosarcoma/malignant fibrous histiocytoma, brain stem glioma, ependymoma, visual pathway and hypothalamic gliomas, breast cancer, bronchial adenomas/carcinoids, carcinoid tumors, gastrointestinal carcinoid tumors, carcinoma, adrenocortical, islet cell carcinoma, primary central nervous system lymphoma, cerebellar astrocytoma, cervical cancer, chronic lymphocytic leukemia, chronic myelogenous leukemia, clear cell sarcoma of tendon sheaths, colon cancer, colorectal cancer, cutaneous t-cell lymphoma, endometrial cancer, ependymoma, esophageal cancer, Ewing's sarcoma/family of tumors, extracranial germ cell tumors, extragonadal germ cell tumors, extrahepatic bile duct cancer, eye cancers, including intraocular melanoma, and retinoblastoma, gallbladder cancer, gastrointestinal carcinoid tumor, ovarian germ cell tumor, gestational trophoblastic tumor, hairy cell leukemia, head and neck cancer, Hodgkin's disease, hypopharyngeal cancer, hypothalamic and visual pathway glioma, intraocular melanoma, Kaposi's sarcoma, laryngeal cancer, acute lymphoblastic leukemia, acute myeloid leukemia, chronic lymphocytic, leukemia, chronic myelogenous leukemia, liver cancer, non-small cell lung cancer, small cell lung cancer, Hodgkin's disease, non-Hodgkin's lymphoma, Waldenstrom's macroglobulinemia, malignant mesothelioma, malignant thymoma, medulloblastoma, melanoma, intraocular melanoma, merkel cell carcinoma, metastatic squamous neck cancer with occult primary, multiple endocrine neoplasia syndrome, multiple myeloma/plasma cell neoplasm, mycosis fungoides, myelodysplastic syndrome, chronic myelogenous leukemia, myeloid leukemia, multiple myeloma, myeloproliferative disorders, nasal cavity and paranasal sinus cancer, nasopharyngeal cancer, neuroblastoma, oral cancer, oral cavity and lip cancer, oropharyngeal cancer, osteosarcoma/malignant fibrous histiocytoma of bone, ovarian cancer, ovarian low malignant potential tumor, pancreatic cancer, paranasal sinus and nasal cavity cancer, parathyroid cancer, penile cancer, pheochromocytoma, pituitary tumor, pleuropulmonary blastoma, prostate cancer, rectal cancer, renal cell (kidney) cancer, transitional cell cancer (e.g. renal pelvis and ureter), retinoblastoma, rhabdomyosarcoma, salivary gland cancer, malignant fibrous histiocytoma of bone, soft tissue sarcoma, sezary syndrome, skin cancer, small intestine cancer, stomach (gastric) cancer, supratentorial primitive neuroectodermal and pineal tumors, cutaneous T-cell lymphoma, testicular cancer, malignant thymoma, gestational trophoblastic tumor, urethral cancer, uterine sarcoma, vaginal cancer, vulvar cancer, and Wilms' tumor.

The method and kit of the invention can be used in conjunction with other methods for diagnosing a growth. Thus, in some embodiments, a portion of a sample obtained using a needle biopsy or surgical biopsy can be used in the method of the invention, while another portion of the same sample can be used in conventional diagnostic and/or prognostic methods, thereby decreasing the need for costly and/or invasive procedures in the subject. In some embodiments, the method and kit of the invention are used in conjunction with conventional histological or cytological examination of the growth.

In some embodiments, the level of midkine present in a sample level is used to assess the grade of a malignancy, to predict disease prognosis, to predict the response to a treatment, and/or to guide the choice of treatment for a growth.

One advantage of the invention is the high sensitivity of the midkine assay, which allows for the determination of the midkine level in a relatively small sample, such as a fine needle aspirate. In some aspects of the invention, the immunoassay for detecting midkine levels includes a step of contacting the sample with a solution comprising (i) an antibody that specifically binds to human midkine and (ii) a polymer. Without wishing to be bound by theory, it is believed that the presence of a polymer during antigen binding increases the affinity or avidity of the anti-midkine antibody for midkine and/or decreases non-specific binding of the anti-midkine antibody to other components present in the sample, thereby increasing the sensitivity of the immunoassay.

The amount of anti-midkine antibody present in the solution is not particularly limited and can be determined empirically by those of skill in the art. In some embodiments, the antibody concentration is 0.01 µg/mL or more, e.g., 0.1 µg/mL or more, 1 µg/mL or more, 5 µg/mL or more, 10 µg/mL or more, or 25 µg/mL or more. Alternatively, or in addition, the antibody concentration is 100 µg/mL or less, e.g., 50 µg/mL or less, 25 µg/mL or less, 10 µg/mL or less, 5 µg/mL or less, 2 µg/mL or less, 1 µg/mL or less, or 0.5 µg/mL or less. Thus, the concentration of anti-midkine antibody present in a solution during antigen binding can be a concentration bounded by any two of the above endpoints. For example, the antibody concentration can be 0.1 µg/mL-5 µg/mL, 1 µg/mL-25 µg/mL, 0.01 µg/mL-1 µg/mL, or 5 µg/mL-10 µg/mL.

In certain embodiments, the immunoassay involves the use of two or more distinct anti-midkine antibodies. The concentration of each anti-midkine antibody for use in a method or kit of the invention can be selected independently by those of skill in the art.

In certain embodiments, the polymer is poly-L-lysine, or a salt or derivative thereof. The amount of poly-L-lysine present in the solution is not particularly limited. In some embodiments, the concentration of poly-L-lysine present in a solution during antigen binding is 0.1 µg/mL or more, e.g., 0.5 µg/mL or more, 1 µg/mL or more, 5 µg/mL or more, 10 µg/mL or more, or 25 µg/mL or more. Alternatively, or in addition, the concentration of poly-L-lysine present in a solution during antigen binding is 1000 µg/mL or less, e.g., 500 µg/mL or less, 250 µg/mL or less, 100 µg/mL or less, 50 µg/mL or less, 20 µg/mL or less, 10 µg/mL or less, or 1 µg/mL or less. Thus, the concentration of poly-L-lysine present in a solution during antigen binding can be a concentration bounded by any two of the above endpoints. For example, the concentration of poly-L-lysine present in a solution during antigen binding can be 0.1 µg/mL-500 µg/mL, 0.5 µg/mL-50 µg/mL, 1 µg/mL-100 µg/mL, or 5 µg/mL-20 µg/mL. In some embodiments, the concentration of poly-L-lysine present in a solution during antigen binding is 10 µg/mL.

The molecular weight of the poly-L-lysine is not particularly limited. In certain embodiments, the poly-L-lysine has an molecular weight of 0.5 kDa-2 kDa, 1 kDa-5 kDa, 4 kDa-15 kDa, 15 kDa-30 kDa, 30 kDa-70 kDa, 70 kDa-150 kDa, or 150 kDa-300 kDa. The poly-L-lysine can be in free base form, or the poly-L-lysine can be in salt form, such as poly-L-lysine hydrochloride or poly-L-lysine hydrobromide.

In some embodiments, the solution comprising an antibody that specifically binds to human midkine contains a polymer which is a derivative of poly-L-lysine. Suitable derivatives of poly-L-lysine include, for example, copolymers of poly-L-lysine and poly-D-lysine, poly-L-lysine conjugated to a protein, and copolymers of poly-L-lysine and poly(ethylene glycol).

In other embodiments, the solution comprising an antibody that specifically binds to human midkine contains a polymer having physiochemical properties similar to poly-L-lysine. Thus, in certain embodiments of the invention, the solution comprising an antibody that specifically binds to human midkine contains another positively charged, water soluble polymer, such as poly-D-lysine or polyarginine.

Although the precise size of a sample is not limiting, a sample for use in the method and kit of the invention can contain as little as 0.1 mg total protein, e.g., 0.5 mg total protein or more, 0.6 mg total protein or more, 0.8 mg total protein or more, 1.0 mg total protein or more, 1.5 mg total protein or more, 3.0 mg total protein or more, 10 mg protein or more, or 25 mg protein or more. Alternatively, or in addition, the sample can contain 200 mg protein or less, e.g., 100 mg total protein or less, 50 mg total protein or less, 30 mg total protein or less, 20 mg total protein or less, 7.5 mg total protein or less, 1 mg total protein or less, or 0.75 mg total protein or less. Thus, the amount of total protein present in a sample for use in the method and kit of the invention can be an amount bounded by any two of the above endpoints. For example, the amount of total protein present in a sample for use in the method and kit of the invention can be 0.1 mg-20 mg, 0.5 mg-7.5 mg, 1.0 mg-100 mg, 3.0 mg-30 mg, or 10 mg-200 mg.

A kit according to the invention comprises at least two components, namely, an anti-midkine antibody and instructional material. In certain embodiments, the kit includes two or more distinct anti-midkine antibodies. The instructional material includes instructions for (a) determining the level of midkine in a sample, and (b) interpreting the results of the determination. Preferably, the instructional material also includes instructions for determining the level of midkine in a control and/or provides one or more control levels (e.g., threshold values) for midkine.

In some embodiments, the instructional material recites a step of contacting the sample with a solution comprising an anti-midkine antibody and a polymer. In certain embodiments, the polymer is poly-L-lysine, or a salt or derivative thereof, as described above in the context of the methods of the invention.

In certain embodiments, the instructional material includes instructions for determining the level of midkine in a sample obtained from a thyroid growth, and diagnosing whether the thyroid growth is benign or malignant.

The kit of the invention can be used in diagnosing a growth obtained from any subject, particularly a mammal. Preferably the mammal is a human. In other embodiments, the mammal can be a mouse, rat, rabbit, cat, dog, pig, sheep, cow, primate, or another mammal.

The sample and the control can be any sample or control suitable for use in the method of the invention as described above.

Pleiotrophin, encoded by the PTN gene in humans, is closely related to midkine by amino acid sequence homology and structural similarity. Pleiotrophin is also known as heparin-binding brain mitogen (HBBM), heparin-binding growth factor 8 (HBGF-8), neurite growth-promoting factor 1 (NEGF1), heparin affinity regulatory peptide (HARP), and heparin binding growth associated molecule (HB-GAM). Together, midkine and pleiotrophin form a family of heparin-binding proteins often referred to as the neurite growth-promoting factor (NEGF) family (Muramatsu et al., *Proc. Jpn. Acad., Ser. B*, 86: 410-425 (2010)).

PTN gene expression is increased in several cancers, including pancreatic carcinoma, choriocarcinoma, neuroblastoma, and melanoma (Muramatsu, *J. Biochem.*, 132: 359-371 (2002)). In addition, serum levels of pleiotrophin are increased in patients with pancreatic and colon carcinoma (Muramatsu, ibid.).

Thus, the invention also provides methods and kits for determining whether a growth is benign or malignant based upon the level of pleiotrophin present in a sample of the growth. In one aspect, the invention provides a method for diagnosing a growth in a subject. The method comprises (a) providing a sample of a growth obtained from a subject, (b) analyzing the sample by an immunoassay to determine the level of pleiotrophin, and (c) comparing the level of pleiotrophin determined from the sample with a control. The level of pleiotrophin determined from the sample as compared with the control is diagnostic of a benign growth or a malignant growth.

In another aspect, the invention provides a kit for diagnosing a growth in a subject. The kit comprises (a) an antibody that specifically binds to human pleiotrophin, and (b) instructional material for determining the level of pleiotrophin by an immunoassay in a sample of a growth from a subject as compared with a control. The level of pleiotrophin determined from the sample as compared with the control is diagnostic of a benign growth or a malignant growth.

The embodiments of the method and kit for determining whether a growth is benign or malignant based upon the level of pleiotrophin present in a sample of the growth are similar to the embodiments of the method and kit described hereinabove with respect to midkine, except that an antibody specific for midkine is substituted for an antibody specific for pleiotrophin.

An antibody specific for pleiotrophin can be generated by any suitable manner known in the art, such as those described herein with respect to the generation of anti-midkine antibodies. The antibody specific for pleiotrophin also can be an anti-pleiotrophin antibody known in the art, such as a commercially available anti-pleiotrophin antibody obtainable from EMD Millipore (Billerica, Mass.) or R&D Systems Inc. (Minneapolis, Minn.). In certain embodiments, the anti-pleiotrophin antibody is a mouse monoclonal anti-pleiotrophin antibody known as 3B10, which is commercially available.

In some embodiments, the method or kit for determining whether a growth is benign or malignant based upon the level of pleiotrophin present in a sample of the growth includes the use of a polymer, such as poly-L-lysine, as described hereinabove with respect to the method and kit based upon midkine. In other embodiments, the method or kit for determining whether a growth is benign or malignant based upon the level of pleiotrophin present in a sample of the growth does not include the use of a polymer.

The following examples further illustrate the invention but, of course, should not be construed as in any way limiting its scope.

EXAMPLE 1

This example demonstrates a method for diagnosing a thyroid nodule by determining the level of midkine in a sample of a thyroid nodule by an immunoassay.

Samples of thyroid tissue were obtained from adult subjects with thyroid nodules who underwent percutaneous fine-needle aspiration (FNA) (n=41), thyroidectomy (n=23), or percutaneous FNA and thyroidectomy (n=9). To obtain the samples, a 25-gauge needle was repeatedly passed into a nodule (either in vivo by percutaneous FNA, or ex vivo immediately after thyroidectomy to mimic percutaneous FNA), and the needle was rinsed with 500 µL phosphate buffered saline (PBS) containing 1% bovine serum albumin (BSA) either before or after expressing a portion of the sample onto a microscope slide for conventional cytological analysis. The rinse (also referred to as a "washout") was aliquotted and stored at −80° C. until immunoassay.

A midkine (MK) sandwich ELISA immunoassay was performed using a commercial kit (BioVendor, Czech Republic) with modifications. 50 µL of thyroid washout was diluted in 200 µL of TBSTA (Tris-buffered saline, 50 mM Tris-HCL, pH 8, 0.15 M NaCl, 0.5% Tween 20, 1% BSA). 100 µL of the diluted samples was transferred in duplicate into a 96-well plate, which was pre-coated by the manufacturer with an anti-midkine capture antibody. The plate was incubated at 37° C. for 2 hours without shaking and then washed 3 times with 0.35 mL per well of the washing buffer provided in the kit. After tapping the inverted plate to remove residual fluid, 10 µg/mL of poly-L-lysine (Sigma-Aldrich, St. Louis, Mo.) in water was added to the biotin-labeled antibody solution provided with the kit, and then 100 &L of this solution was added to each well. The plate was incubated at room temperature for 1 hour, with shaking at 300 RPM on an orbital microplate shaker. Then the wells were washed 5 times with 0.35 mL per well of the washing buffer provided in the kit. After tapping, 100 µL of streptavidin-HRP conjugate solution provided with the kit was added to each well. The plate was incubated at room temperature for 30 minutes, with shaking at 300 RPM on an orbital microplate shaker. After washing 5 times with washing buffer and tapping, the substrate solution provided with the kit was added to each well. The plate was covered with aluminum foil and incubated for 7 minutes at room temperature. Color development was stopped by adding 100 µL per well of the stop solution provided with the kit. The absorbance of each well at 450 nm was measured using a microplate reader. Intra-assay CV was 3.4% for high concentration and 5.2% for low concentration. The limit of detection was 8.7 pg/mL midkine. The absolute concentration of midkine in a sample was calculated by comparison to a control, which consisted of multiple dilutions of recombinant human midkine of known concentrations.

A thyroglobulin (Tg) assay also was performed on an aliquot of each washout. Briefly, an aliquot of each washout was diluted 10-fold in normal saline, and the thyroglobulin concentration was measured with a chemiluminescent immunometric assay (Immulite 2000XPi, Siemens, UK) according to the manufacturer's instructions. Thyroglobulin reagent (Siemens Healthcare Diagnostics, USA) was used to further dilute each sample, if needed.

The midkine concentrations or the midkine to thyroglobulin ratios (MK/Tg) of multiple needle passes were averaged for each subject. Statistical analysis was performed using SigmaPlot software, version 12. The relationship between midkine and thyroglblulin concentrations was analyzed by regression. Midkine and MK/Tg were compared in benign versus malignant nodules by T-test. For this analysis, all FNA samples (separate passes of the needle) were averaged to obtain a single mean for each subject. For subjects with both in vivo and ex vivo samples, only the in vivo values were included, which are more relevant clinically. P values <0.05 were considered significant.

Figure 1:
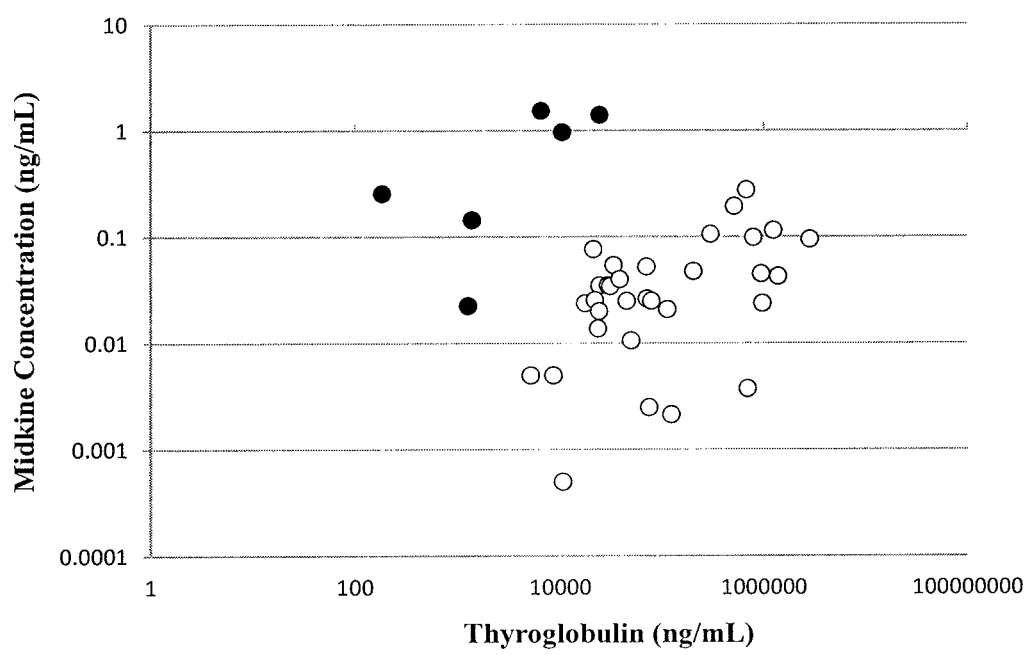
FIG. 1 is a dot plot depicting midkine and thyroglobulin concentrations in fine-needle aspirate (FNA) samples of histologically confirmed benign thyroid nodules (open circles) or papillary thyroid cancer (PTC) (closed circles).

For normal thyroid tissue samples (obtained ex vivo from thyroid gland distant from any nodule), washout of the FNA needle contained very low concentrations of MK (0.03±0.01 ng/mL). MK concentrations were also low in samples obtained ex vivo from nodules that were benign by surgical pathology (0.07±0.02 ng/mL) and samples obtained in vivo from nodules with benign cytology (0.02±0.01 ng/mL). In the subjects with surgically confirmed benign nodules, MK concentrations were similarly low in adenomatoid/colloid nodules (0.027±0.016 ng/mL, n=12), follicular adenomas (0.079±0.073 ng/mL, n=3), and benign nodules with underlying chronic lymphocytic thyroiditis (0.008±0.007 ng/mL, n=5). MK concentrations from subjects with Graves' disease also were low (0.062±0.013 ng/mL, n=3). In contrast, MK concentrations in samples from papillary thyroid cancer (PTC) showed higher levels than in benign nodules (0.72±0.27 ng/mL versus 0.03±0.01 p=0.006), irrespective of whether the samples were obtained in vivo or ex vivo (FIG. 1). Conversely, thyroglobulin concentrations were lower in samples of PTC than in samples of benign nodules (7540±4600 ng/mL versus 110000±28900 ng/mL, p<0.001) (FIG. 1).

The results of this example demonstrate that midkine protein levels in FNA washout samples are higher in papillary thyroid cancer than in normal thyroid tissue or benign thyroid nodules.

EXAMPLE 2

This example demonstrates a method for diagnosing a thyroid nodule by determining the ratio of midkine to thyroglobulin in a sample of a thyroid nodule.

Midkine to thyroglobulin (MK/Tg) ratios were calculated based upon the results of the assays described in Example 1. MK concentration was positively associated with thyroglobulin concentrations in FNA washout samples from both benign and malignant nodules ($R^2$=0.09, p<0.001 and $R^2$=0.53, p<0.001, respectively). This correlation likely occurs because both MK and thyroglobulin concentrations in the washout fluid are dependent on the amount of thyroid tissue present in the sample. Therefore, to correct for the amount of thyroid tissue, midkine levels were normalized to thyroglobulin levels by calculating the MK/Tg ratio. In subjects with both in vivo and ex vivo samples, the MK/Tg ratio was similar in the two types of samples (1.81±0.95 ng/mg versus 1.74±0.70 ng/mg, respectively for benign nodules, p=NS).

Figure 2:
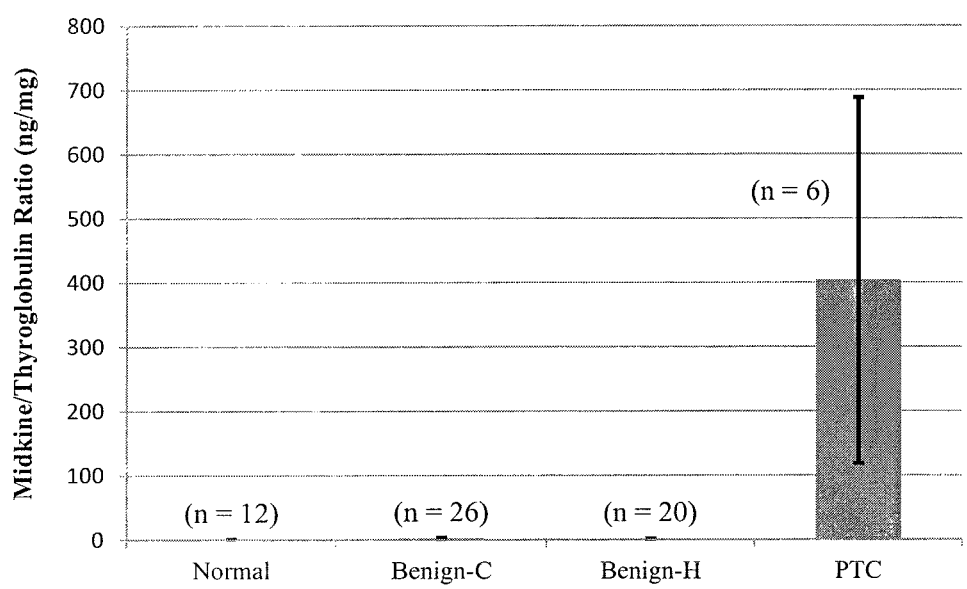
FIG. 2 is a bar graph depicting midkine to thyroglobulin ratio (MK/Tg, mean±SEM) in FNA samples of benign thyroid nodules or malignant papillary thyroid cancer (PTC). Thyroid nodules found to be benign by cytology only (Benign-C) are shown separately from those found to be benign by postoperative histology (Benign-H).

Samples from normal thyroid tissue and Graves' disease showed low midkine to thyroglobulin ratios. Similarly low values were seen for benign nodules, which included adenomatoid/colloid nodules, follicular adenomas, and benign nodules within a thyroid affected by chronic lymphocytic thyroiditis. In contrast, the MK/Tg ratio was far higher in papillary thyroid cancer (PTC) samples than in benign nodules (403±285 ng/mg versus 1.51±0.55 ng/mg, P<0.001, for subjects with a histological diagnosis) (FIG. 2). The MK/Tg ratio tended to increase with nodule size in PTC, but the relationship did not reach statistical significance ($R^2=0.51$, P=0.09).

For the preceding analysis, all FNA samples (separate passes of the needle) were averaged for each subject. To assess the sampling variability in the MK/Tg ratio, individual FNA samples from the same malignant lesion were compared. There was a reasonably close agreement among individual samples, and all individual MK/Tg ratios were substantially higher than the MK/Tg ratios determined from benign lesions (FIG. 3).

The results of this example demonstrate that midkine to thyroglobulin ratios in FNA washout samples are higher in papillary thyroid cancer than in normal thyroid tissue or benign thyroid nodules.

EXAMPLE 3

This example demonstrates a method of increasing the sensitivity of an immunoassay for determining the level of midkine in a sample.

A midkine sandwich ELISA immunoassay was performed using a commercial kit (BioVendor, Czech Republic) as described in Example 1, except that recombinant human midkine at a concentration of 0, 0.033, 0.1, 0.3, 0.9 ng/mL was prepared in 200 µL of TBSTA instead of a thyroid washout. Increasing concentrations of recombinant human midkine produced increasing signal in the sandwich ELISA (FIG. 4). Addition of 10 µg/mL poly-L-lysine (PLL) to the detection antibody solution markedly increased the overall absorbance values at each midkine concentration as well as the slope of the response curve (FIG. 4).

The results of this example demonstrate that the addition of poly-L-lysine to a solution containing an antibody specific for midkine increases the sensitivity of an immunoassay.

EXAMPLE 4

This example demonstrates a method for diagnosing a thyroid nodule by determining the level of pleiotrophin in a sample of a thyroid nodule by an immunoassay.

Samples of thyroid tissue were obtained from adult subjects with thyroid nodules who underwent thyroidectomy (n=31). After the thyroid was excised, the nodules of interest were identified by the surgeon and pathologist, and the selected nodules with surrounding tissues were bisected for procurement. 25 benign nodules from 23 subjects and 10 nodules with PTC from 8 subjects were identified by histological analyses. No follicular, medullary, or anaplastic thyroid cancers were identified by histological analyses. 2 subjects had underlying Graves' disease. 1 subject with benign nodules had underlying chronic lymphocytic thyroiditis.

Ex vivo fine-needle aspiration (FNA) was performed by repeatedly passing a 25-gauge needle into a nodule to mimic percutaneous FNA. The needle was rinsed with 500 µL phosphate buffered saline (PBS) containing 1% bovine serum albumin (BSA) to obtain washout samples, which were aliquotted and stored at −80° C. until immunoassay. Multiple ex vivo FNA samples (mean of 3.0 passes) were obtained per nodule. Normal thyroid tissue samples were obtained from 11 subjects by performing ex vivo FNA on normal thyroid tissue adjacent to benign or malignant nodules.

A pleiotrophin sandwich ELISA immunoassay was performed using a mouse anti-pleiotrophin monoclonal antibody (3B10, available from EMD Millipore, Billerica, Mass.) and a biotinylated anti-human pleiotrophin goat IgG (available from R&D Systems, Inc., Minneapolis, Minn.). The 3B10 antibody was diluted to 0.5 µg/mL in PBS, and 100 µL/well was incubated in a 96-well plate at 4° C. overnight. The wells were washed 3 times with 250 µL per well PBST (PBS, 0.05% TWEEN™ 20). The wells were blocked with 250 µL per well of PBS containing 3% BSA and 0.2% TWEEN™ 20 for 2 hours at 4° C. Without washing, the plate was inverted and dried by tapping vigorously against a paper towel. 100 µL of thyroid washout sample was diluted in 200 µL of PBSTA (PBS, 1% BSA, 0.5% TWEEN™ 20). 100 µL of the diluted sample was transferred, in duplicate, into the plate. The plate was incubated with gentle agitation at room temperature for 2 hours, and then washed 3 times with 250 µL per well of PBST. After tapping the inverted plate to remove residual fluid, the biotinylated anti-human pleiotrophin goat IgG was added at a concentration of 500 ng/mL and diluted in a 0.9% normal saline containing 5.7 mEq/L calcium chloride and 0.5% BSA, at pH 6. The plate was incubated with gentle agitation at room temperature for an hour. The wells were washed 5 times with 250 µL of PBST per well. After tapping the inverted plate to remove residual fluid, 100 µL streptavidin-HRP conjugate solution (Thermo Scientific, Rockford, Ill.) was added at a concentration of 25 ng/mL in PBS to each well, and the plate was incubated at room temperature for 30 minutes with gentle agitation. After washing 5 times with PBST, 100 µL of 3,3',5,5'-tetramethylbenzidine (TMB) was added to each well. The plate was covered with aluminum foil and incubated for 7 minutes at room temperature. Color development was stopped by adding 100 µL of stop solution. The absorbance of each well at 450 nm was measured using a microplate reader. The intra-assay CV was 5.1% for high concentration and 7.3% for low concentration. The inter-assay CV was 6.4%. The absolute concentration of pleiotrophin in a sample was calculated by comparison to a control, which consisted of multiple dilutions of recombinant human pleiotrophin of known concentrations.

A thyroglobulin (Tg) assay also was performed on an aliquot of each washout. Briefly, 50 µL of thyroid washout sample was diluted 10-fold in normal saline, and the thyroglobulin concentration was measured with a chemiluminescent immunometric assay (Immulite 2000XPi, Siemens, UK) according to the manufacturer's instructions. Thyroglobulin reagent (Siemens Healthcare Diagnostics, USA) was used to further dilute each sample, if needed.

The pleiotrophin (PTN) concentrations or the pleiotrophin to thyroglobulin ratios (PTN/Tg) of multiple needle passes were averaged to obtain a single mean value for each nodule. Statistical analysis was performed using SigmaPlot software, version 12. The relationship between pleiotrophin and thyrogloblulin concentrations was analyzed by Pearson correlation after log transformation of both variables. Pleiotrophin and PTN/Tg were compared in benign versus malignant nodules by T-test. P values <0.05 were considered significant.

The mean concentration of PTN in normal thyroid tissue was 29±13 pg/mL. PTN concentrations in samples from PTC tissue were higher than in samples from benign nodules (85±25 pg/mL versus 35±11 pg/mL, mean±SEM, p=0.01) (Table and FIG. 5). Conversely, thyroglobulin concentrations in samples from PTC tissue were lower than in samples from benign nodules (59.4±24 μg/mL versus 664±146 μg/mL, p=0.008) (Table and FIG. 5).

The PTN and PTN/Tg values, along with the pathology results, are set forth in the following Table.

TABLE

Pleiotrophin and pleiotrophin/thyroglobulin ratio with pathology results

|  |  | PTN (pg/mL) Mean ± SD | PTN/Tg ratio (pg/mg) Mean ± SD |
|---|---|---|---|
| Surgical Pathology - Benign | N = 25 |  |  |
| Adenomatoid/Nodular hyperplasia | 19 | 38 ± 65 | 118 ± 261 |
| Autoimmune thyroiditis | 1 | 0 | 0 |
| Follicular adenoma | 3 | 15 ± 21 | 54 ± 76 |
| Focal epithelial hyperplasia/Graves | 1 | 74 | 2334 |
| Nodular hyperplasia/Graves | 1 | 40 | 1639 |
| All benign nodules | 25 | 35 ± 11 | 357 ± 145 |
| Surgical Pathology - PTC | N = 8 |  |  |
| Classic | 2 | 86 ± 48 | 19500 ± 26700 |
| Tall cell | 3 | 115 ± 109 | 10900 ± 8250 |
| Follicular variant | 2 | 61 ± 23 | 724 ± 186 |
| Unclassified | 1 | 20.6 | 2949 |
| All malignant nodules | 8 | 85 ± 25 | 9490 ± 4730 |

The results of this example demonstrate that pleiotrophin levels in FNA washout samples are higher in papillary thyroid cancer tissue than in normal thyroid tissue or benign thyroid nodules.

EXAMPLE 5

This example demonstrates a method for diagnosing a thyroid nodule by determining the ratio of pleiotrophin to thyroglobulin in a sample of a thyroid nodule.

Pleiotrophin to thyroglobulin (PTN/Tg) ratios were calculated based upon the results of the assays described in Example 4. The mean PTN/Tg ratio in normal thyroid tissue was 2950±888 pg/mg. The PTN/Tg ratio values were low in benign nodules, including adenomatoid/colloid nodules, follicular adenomas, and benign nodules within a thyroid affected by chronic lymphocytic thyroiditis (FIGS. 6A and 6B). The PTN/Tg ratio values were higher in papillary thyroid cancer tissue than in benign nodules (9490±4730 pg/mg versus 357±145 pg/mg, p<0.001) (FIGS. 6A and 6B). The PTN/Tg ratio did not appear to correlate with nodule size. Samples from benign nodules obtained from patients with Graves' disease showed high pleiotrophin to thyroglobulin ratios (FIG. 6B).

The results of this example demonstrate that pleiotrophin to thyroglobulin ratios in FNA washout samples are higher in papillary thyroid cancer tissue than in benign thyroid nodules.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a growth in a subject comprising:
   (a) providing a sample of a growth obtained from thyroid tissue of a subject,
   (b) analyzing the sample by an immunoassay to determine the concentration of pleiotrophin protein in the sample,
   (c) analyzing the sample by an immunoassay to determine the concentration of thyroglobulin protein in the sample,
   (d) determining the ratio of pleiotrophin protein concentration to thyroglobulin protein concentration (PTN/Tg) in the sample,
   (e) comparing the ratio of pleiotrophin protein concentration to thyroglobulin protein concentration determined from the sample with a control,
   (f) providing a diagnosis of the growth as a malignant growth after determining an increased ratio of pleiotrophin protein concentration to thyroglobulin protein concentration determined from the sample as compared to the control and (g) performing a thyroidectomy on the subject,
wherein the control is the ratio of pleiotrophin protein concentration to thyroglobulin protein concentration in a benign growth.

2. The method of claim 1, wherein the growth is a thyroid nodule.

3. The method of claim 1, wherein the growth is a tumor.

4. The method of claim 1, which further comprises histological or cytological examination of the growth.

5. The method of claim 1, wherein the immunoassay of (b) is a sandwich enzyme-linked immunosorbent assay (ELISA) which comprises a step of contacting the sample with a solution comprising an antibody that specifically binds to human pleiotrophin protein.

6. The method of claim 5, wherein the antibody is conjugated to a label that is biotin, a radionuclide, a fluorescent molecule, a chemiluminescent molecule, or an enzyme.

7. The method of claim 5, wherein the solution comprises a polymer.

8. The method of claim 7, wherein the polymer is poly-L-lysine.

9. The method of claim 8, wherein the concentration of poly-L-lysine in the solution is 10 μg/mL.

* * * * *